United States Patent [19]

Okamoto et al.

[11] Patent Number: 4,880,629

[45] Date of Patent: Nov. 14, 1989

[54] DIALYTIC SOLUTION FOR PERITONEAL DIALYSIS

[75] Inventors: Takeshi Okamoto, Kawagoe; Mitsuo Iwata, Sagamihara; Hiroaki Takahashi, Tokyo, all of Japan

[73] Assignee: Terumo Kabushiki Kaisha, Trading as TERUMO CORPORATION, Tokyo, Japan

[21] Appl. No.: 855,343

[22] Filed: Apr. 24, 1986

[30] Foreign Application Priority Data

Apr. 25, 1985 [JP] Japan .................................. 60-87621

[51] Int. Cl.$^4$ ...................... A61K 31/14; A61K 31/17
[52] U.S. Cl. ...................................... 424/678; 514/23; 424/680; 424/717
[58] Field of Search ................. 127/54, 30; 210/321.2; 594/23; 424/153

[56] References Cited

FOREIGN PATENT DOCUMENTS

WO82/03987  11/1982  PCT Int'l Appl.

OTHER PUBLICATIONS

Lindholm, B. et al, "Glycerol as Osmotic Agent in Peritoneal Dialysis (PD)", *Artificial Organs*, vol. 7(A), Nov., 1983, p. 47.

Yuasa, S. et al., "Clinical Evaluation of Peritoneal Dialysis with Glycerol Dialysate", (English abstract), *Toseki Kaishi*, vol. 14(5), 1981, pp. 279–284.

Arakawa, M., "Hemolytic Action of Glycerol and Antihemolytic Action of Fructose", (English Abstract), *Journal of Japan Pharmacology Society*, vol. 73, 1977, pp. 541–547.

*Primary Examiner*—Stanley J. Friedman
*Attorney, Agent, or Firm*—Burns, Doane, Swecker & Mathis

[57] ABSTRACT

A dialytic solution for peritoneal dialysis, which dialytic solution is characterized by containing glycerol and a monosaccharide as osmotic pressure regulating agents for regulating the osmotic pressure to a level necessary for the removal of water.

5 Claims, 1 Drawing Sheet

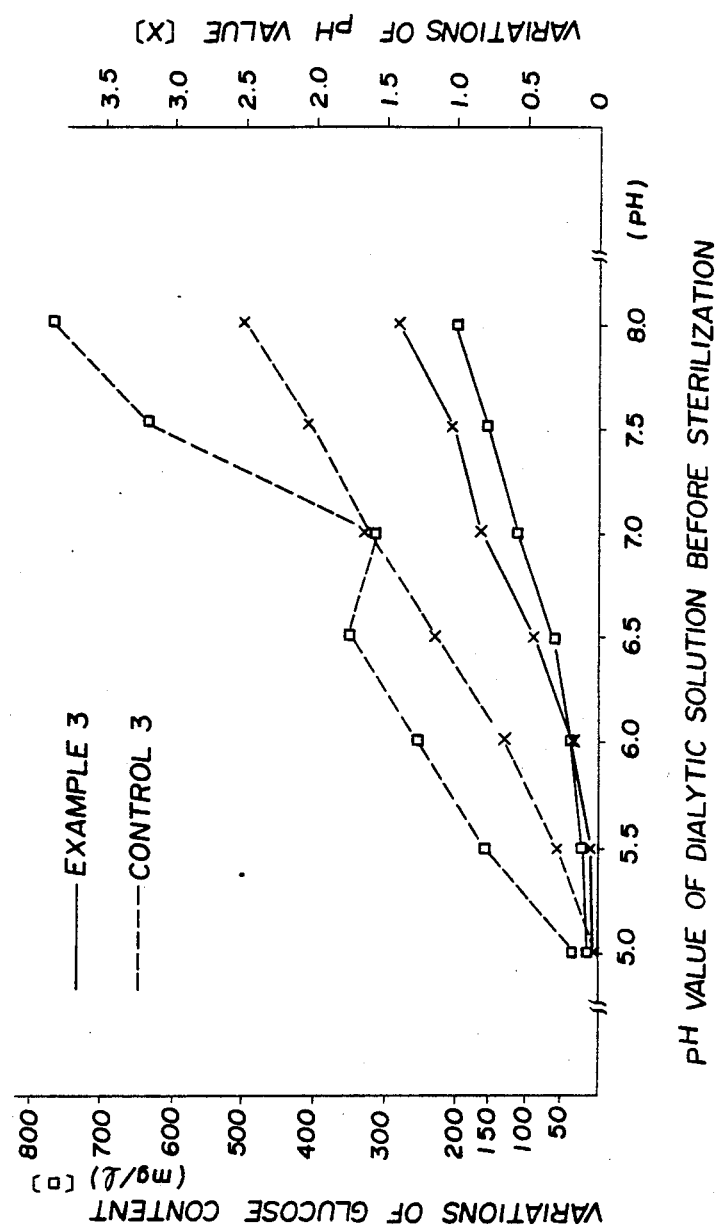

DIALYTIC SOLUTION FOR PERITONEAL DIALYSIS

BACKGROUND OF THE INVENTION

1. Field of the Invention

This invention relates to a dialytic solution for peritoneal dialysis. More particularly, this invention relates to a dialytic solution for peritoneal dialysis, which is free from the danger latent in the load exerted on the patient by an osmotic pressure regulating agent contained in the dialytic solution.

2. Description of the Prior Art

As one method for the treatment of patients suffering from renal failure or from intoxication with poisons or violent substances, the dialytic therapy has been in application for a long time. Broadly, this dialytic therapy is divided into hemodialysis and peritoneal dialysis. The hemodialysis is effected by drawing the patient's blood out of his body, introducing the blood into an artificail kidney, i.e. a dialyzer provided with an artificial dialytic membrane, allowing metabolic wastes contained in the blood to diffuse through the artificial membrane and pass into a washing perfusing solution, and removing excess water through ultrafiltration utilizing the pressure adjusted with an external circulating device. The peritoneal dialysis is effected by directly injecting a dialytic solution into the patient's abdominal cavity, allowing the metabolic wastes contained in the blood to diffuse through the peritoneum and pass into the dialytic solution, and removing excess water by virtue of the difference in the osmotic pressure produced between the injected hypertonic dialytic solution and the body fluid.

For the dialytic therapy, the hemodialysis has chiefly found application to date because the peritoneal dialysis is liable to induce peritonitis. The peritoneal dialysis has been selectively adopted for cases of blood access trouble, complications, and senility for which the hemodialysis is not suitable. The hemodialysis has been demonstrated to permit elongation of the patient's life by not less than 20 years on the condition that it is applied smoothly. Further the fact that most patients under sustained treatment of hemodialysis visit hospitals regularly for the treatment apparently indicates that this therapy contributes appreciably to the patient's return to normal social life. The hemodialysis in current use, however, does not prove fully satisfactory. For example, it does not infrequently, induce such uncontrollable complications as insufficient immunity, anemia, nutritional disorder, bone trouble, dysarteritony, and vascular sclerosis. Further, the patients find their regular visits to hospitals for protracted periodic treatments troublesome. Moreover, part of the diseases induced by the therapy of hemodialysis are treated by existing methods intermittently at the rate of two or three times a week. These diseases are undeniably ascribable to the fact that the dialytic membranes and the dialytic solutions currently in use are deficient in vital adaptability.

Recently, the continuous ambulatory peritoneal dialysis (CAPD) has been established as one form of the peritoneal dialysis. This CAPD is rapidly disseminating as one method of dialytic therapy. This is because the CAPD which comprises keeping a dialytic solution retained at all times within the abdominal cavity, repeating discharge and injection of the dialytic solution at intervals of 4 to 8 hours, and thus using 4 to 10 liters of the dialytic solution daily provides eficient dialysis, because the dialysis constitutes itself a sustained treatment, because the dialysis exerts no heavy physiological load upon the patient, because the peritoneum excels the artificial dialytic membrane in the removal of medium to high molecular weight solutes and, therefore, the problem of vital adaptability inherent in the artificial membrane is not encountered, because the dialytic solution to be used can be of a far more refined grade, because the dialysis has no use for any large apparatus and is relatively simple to operate and, therefore, suits home treatment, because the patient is allowed to decrease the frequency of hospital visit and enjoys a reduction in the expense of treatment, and because burden of dietary restriction is lessened. Besides these advantages which the hemodialysis fails to offer, the CAPD promises elimination of part of the disease inherently induced by the hemodialysis and further factilitates the patient's return to normal social life.

There are indications that the peritoneal dialysis centering on the CAPD will occupy an increasingly important position as one method for the purification of blood in the future.

The dialytic solutions used for the peritoneal dialysis are varied in minute details by the difference in the manner of peritoneal dialysis as between the CAPD and the intermittent peritoneal dialysis (IPD). Basically, however, they are similar in respect that they invariably comprise electrolytes represented by $Na^+$ ion, $Ca^{2+}$ ion, $Mg^{2+}$ ion, and $Cl^-$ ion, alkalinizing agents typified by lactate and acetate, and osmotic pressure regulating agents. In Table 1, the basic compositions of the peritoneal dialytic solutions currently in general use or in clinical use are shown in comparison with the composition of blood plasma.

TABLE 1

| Name | pH | Na (mEq/l.) | Ca (mEq/l.) | Mg (mEq/l.) | Cl (mEq/l.) | Lactate (mEq/l.) | Glucose (mg/dl) | Osmotic pressure (mOsm/l.) |
|---|---|---|---|---|---|---|---|---|
| Perisorita*1 | | 140 | 4.5 | 1.5 | 101 | 45 | 1300 | 361.2 |
| Perisorita (G)*1 | | 140 | 4.5 | 1.5 | 101 | 45 | 7000 | 677.9 |
| Perisorita Na 130*1 | | 130 | 4.5 | 1.5 | 98 | 38 | 1600 | 357.9 |
| Perisorita Na 130 (G)*1 | | 130 | 4.5 | 1.5 | 98 | 38 | 7000 | 657.9 |
| EL Reflac No. 1 *2 | | 140 | 4.0 | 1.5 | 102 | 43 | 1500 | 371.0 |
| EL Reflac No. 2 *2 | | 140 | 4.0 | 1.5 | 102 | 43 | 7000 | 676.6 |
| CAPD-135 *3 | 5.5 | 135 | 4.0 | 1.5 | 105.5 | 35 | 1350 | 355 |
| CAPD-250 *3 | 5.5 | 135 | 4.0 | 1.5 | 105.5 | 35 | 2500 | 419 |
| CAPD-400 *3 | 5.5 | 135 | 4.0 | 1.5 | 105.5 | 35 | 4000 | 500 |

TABLE 1-continued

| | | Basic composition of dialytic solution for peritoneal dialysis (theoretical) | | | | | | |
|---|---|---|---|---|---|---|---|---|
| Name | pH | Na (mEq/l.) | Ca (mEq/l.) | Mg (mEq/l.) | Cl (mEq/l.) | Lactate (mEq/l.) | Glucose (mg/dl) | Osmotic pressure (mOsm/l.) |
| Plasma | 7.4 | 140 | 5.0 | 1.5 | 100 | | 100 | 280 |

*1: Shimizu Pharmaceutical
*2: Morishita Pharmaceutical
*3: Terumo K. K.

In the peritoneal dialysis as described above, since the difference in osmotic pressure between the body fluid and the dialytic solution is utilized for the removal of excess water contained in the body fluid, the osmotic pressure of the dialytic solution for the peritoneal dialysis must be maintained at a higher level than that of the patient's blood plasma. Thus, the dialytic solution for the peritoneal dialysis is required to incorporate therein an osmotic pressure regulating agent, i.e. a solute for hightening the osmotic pressure thereof. Generally, as the osmotic pressure regulating agent, glucose is used as mentioned above. The solute which is contained as the osmotic pressure regulating agent in the dialytic solution for the peritoneal dialysis is diffused through the peritoneum into the body fluid by entirely the same mechanism as the metabolic wastes contained in the body fluid, specifically such electrolytes as Na+ ion and Cl− ion and such solutes as urea and creatinine are diffused through the peritoneum into the dialytic solution for the peritoneal dialysis. In fact, the glucose content of the electrolytic solution decreases with the lapse of time when the electrolytic solution is actually used for the peritoneal dialysis. When the glucose is used as the osmotic pressure regulating agent in the dialytic solution for the peritoneal dialysis as described above, therefore, the peritoneal dialysis causes sustained absorption of the glucose into the patient's body. This forced assimilation of the high-calorie sugar by the peritoneal dialysis has the latent danger of exposing the patient to aggravation of corpulence, arteriosclerosis, compelling the patient of diabetes to strive for maintenance of blood sugar content, and inducing accelerated complication of various diseases.

Various studies are now under way for the purpose of overcoming the disadvantages caused by the glucose contained in the dialytic solutions currently in common use for the peritoneal dialysis. For example, use of glycerol as an osmotic pressure regulating agent in the place of glucose has been proposed [S. Yuasa et al: "Clinical evaluation of peritoneal dialysis with glycerol dialysate," Toseki Kaishi, 14, 279–284, 1981 (5); D. E. Ralph et al.: "Dialysis soln. contg. glycerol and opt. amino acid source, esp. for ambulatory peritoneal dialysis,"; U.S. Pat. Ser. No. 263,818 (corresponding to Japanese Patent Application SH No. 56(1981)-187,674), B. Lindholm et al: "Glycerol as osmotic agent in perinoteal dialysis (PD)"; Artificial Organs, 7A, 47, 1983 (November)]. Since glycerol has a small molecular weight, specifically about one half of the molecular weight of glucose, it permits required adjustment of the osmotic pressure at a low application rate and lessens the caloric burden on the patient. Glycerol has no use for insulin in completing its main path of metabolism and undergoes metabolism quickly and completely. It has only a sparing possibility of increasing the blood sugar level. Thus, glycerol enjoys various advantages not found in glucose. Lindholm et al. pointed out in their report that since glycerol has a small molecular weight as compared with glucose and diffuses quickly through the peritoneum into the patient's body, the osmotic pressure required for the removal of excess water during the sustained retention of the dialytic solution within the abdominal cavity cannot be maintained for a long time. We, in our qualitative animal (rat) test using glucose and glycerol, have confirmed the same trend as Lindholm et al. It has been known for a long time that animals, when parenterally given large doses of glycerol, discharge hemoglobinuria. It is generally held that the manifestation of hemoglobin is ascribed to the red blood-corpuscles in the blood [V. Johnson, A. J. Carlson, and A. Johnson: "Am. J. Physiol.," 103, 517, 1933; G. R. Cameron and E. S. Fingkh: "J. Path. Bact.," 51, 165, 1956; A. J. Spiegel and M. M. Noseworthy: "J. Pharm. Sci.," 52, 917, 1963]. The hemolytic action of glycerol is interpreted as a phenomenon that the glycerol cause part of the lipid of the erythrocytic membrane to be dissolved out into the solute and includes dehydration of the erythrocytic membrane [Masayuki Arakawa: "Hemolytic action of glycerol and antihemolytic action of fructose, "Journal of Japan Pharmacology Society, 73, 514–547, 1977]. We have conducted an animal (rat) test on the intra-abdominal administration of highly concentrated glycerol solution based on the prior knowledge mentioned above to find that in the group of rats given a dose of 10 g/dl of glycerol, conspicuous hemolysis is recognized 10 minutes after the administration when the glycerol concentration in the serum is 163 mg/dl. It has been further observed that this degree of hemolysis varies with the lapse of time, reaching its peak 60 minutes after the administration when the glycerol concentration in the serum is 250 mg/dl and persisting until 180 minutes after the administration when the glycerol concentration in the serum is 181 mg/dl. In an additional test, it has been learned that similar results are obtained in the group of rats intra-abdominally given glycerol in such doses that the glycerol concentrations in the serum exceed the level of 150 to 200 mg/dl. These results of the additional test conducted by the inventors suggest that the hemolytic action of glycerol is possibly produced not only by the direct injection into the blood such as the intravenous injection but also by the intra-abdominal administration. It is said that the hemolytic action of glycerol is heavily affected by the difference in species and the human red-blood corpuscles are relatively less susceptible to the hemolytic action. In the light of the mechanism of the hemolysis to be reasonably assumed, the latent danger involved when a dialytic solution containing glycerol as an osmotic pressure regulating agent which is used a long time for peritoneal dialysis cannot be ignored.

This invention, therefore, aims to solve the problem mentioned above.

To be specific, an object of this invention is to provide an improved dialytic solution for peritoneal dialysis.

Another object of this invention is to provide a dialytic solution for peritoneal dialysis, which has no latent danger in the load exerted upon the patient by an osmotic pressure regulating agent contained in the dialytic solution for peritoneal dialysis.

A further object of this invention is to provide a dialytic solution for peritoneal dialysis, which permits highly safe protracted use and proves particularly advantageous for the purpose of CAPD.

SUMMARY OF THE INVENTION

The objects described above are accomplished by a dialytic solution for peritoneal dialysis, which dialytic solution contains glycerol and a monosaccharide as osmotic pressure regulating agents for regulating the osmotic pressure necessary for the removal of water.

This invention also discloses a dialytic solution for peritoneal dialysis, which has a human metabolic monosaccharide as the monosaccharide. This invention further discloses a dialytic solution for peritoneal dialysis, which contains a plurality of monosaccharides as the monosaccharide. This invention further discloses a dialytic solution for peritoneal dialysis, which contains at least glucose as the monosaccharide. This invention further discloses a dialytic solution for peritoneal dialysis, which contains at least glucose as the monosaccharide. This invention further discloses a dialytic solution for peritoneal dialysis, which contains glucose and fructose as the monosaccharide. This invention further discloses a dialytic solution for peritoneal dialysis, which contains 0.5 to 40 g of glycerol and 0.005 to 78 g of a monosaccharide per liter. This invention further discloses a dialytic solution for peritoneal dialysis, which contains 0.5 to 40 g of glycerol, 0.005 to 78 g of glucose, and 0.005 to 78 g of fructose per liter. This invention further discloses a dialytic solution for peritoneal dialysis, which contains 130 to 140 mEq. of $Na^+$ ion, 100 to 140 mEq. of $Cl^-$ ion, 0 to 8 mEq. of $Ca^{2+}$ ion, and 0 to 4 mEq. of $Mg^{2+}$ ion. This invention further discloses a dialytic solution for peritoneal dialysis, which contains 30 to 50 mEq. of at least one bicarbonate precursor ion selected from the group consisting of bicarbonates, lactic acid, acetic acid, malic acid, and succinic acid per liter. Besides, this invention discloses a dialytic solution for peritoneal dialysis, which has an osmotic pressure in the range of 280 to 700 m Osm/lit. This invention also discloses a dialytic solution for peritoneal dialysis, which has a pH in the range of 5.5 to 6.5.

BRIEF DESCRIPTION OF THE DRAWINGS

The drawing illustrates the relation between the variations of glucose content and pH value of the dialytic solution caused by the sterilization in an autoclave and the pH value of the dialytic solution.

DESCTIPTION OF THE PREFERRED EMBODIMENT

The strongest characteristic of this invention resides in using glycerol and a monosaccharide in combination as osmotic pressure regulating agents in the dialytic solution for peritoneal dialysis. Heretofore, it has been proposed to use glycerol as an osmotic pressure regulating agent for the purpose of eliminating the problem that excess glucose is wholly absorbed as an energy source and, because of the reducing group possessed by glucose, the dialytic solution having the pH thereof closely approximated to the physiological level (pH 7.4) is deprived of stability by the high temperature used during the sterilization in the autoclave. In this case, it has been held desirable that glycerol completely replaces glucose, i.e. that absolutely no glucose is contained in the dialytic solution for peritoneal dialysis. It has now been found that in view of the hemolytic property exhibited by glycerol on the red-blood corpuscles, the inclusion of a certain amount of saccharide solution proves rather desirable than otherwise for the sake of the dialytic solution for peritoneal dialysis because it is capable of inhibiting the hemolytic activity of glycerol. It has been further confirmed that the amount of the saccharide to be so contained is small because of the combined use of glycerol and, therefore, is incapable of substantially affecting the elevation of blood sugar value and that although it is important for the pH value of the dialytic solution of the peritoneal dialysis to be closely approximated to the physiological level, the dialytic solution which has a pH exceeding a certain level such as, for example, 5.5 refrains from manifesting any intraabdominal stimulating property similar to the dialytic solution of a physiological pH level.

Now, the present invention will be described in further detail below.

This invention is directed to a diayltic solution for peritoneal dialysis, which dialytic solution is characterized by containing glycerol and a monosaccharide as osmotic pressure regulating agents for regulating the osmotic pressure to a level necessary for the removal of water.

It is known that when the monosaccharide is added to a glycerol solution and the resulting mixture is injected directly into the veins or into the blood in vitro, the monosaccharide has an effect of precluding glycerol from manifesting a hemolytic activity (Masayuki Arakawa: "Hemolytic action of glycerol and antihemolytic action of fructose," ibidem). It has now been found that the monosaccharide functions to prevent glycerol from manifesting a hemolytic activity also when it is administered intraabdominally in combination with glycerol. There does not need to be only one monosaccharide that is added to the dialytic solution for peritoneal dialysis. A plurality of monosaccharides may be added at the same time. Particularly when a plurality of monosaccharides are added, the produced dialytic solution can be expected to have an effect of lightening the burden imposed by each of the monosaccharides upon the patient because the amount in which each of the monosaccharides is required to be used for the purpose of attaining the prescribed osmotic pressure is smaller than when only one monosaccharide is added. These monosaccharides are desired to be such monosaccharides as glucose, fructose, mannose, and galactose which can be metabolized in human bodies. For example, when the dialytic solution for peritoneal dialysis is protracted use and when the monosaccharide used in the dialytic solution lacks metabolism in human bodies, there ensue the possibility that the monosaccharide which has passed from the dialytic solution for peritoneal dialysis into the human body will accumulate in the body to the extent of causing some harm to the patient and the possibility that the monosaccharide is suffered to accumulate in the body, the osmotic pressure in the body will build up even to the extent of preventing the dialytic system from normally functioning. As the monosaccharide, the dialytic solution is desired to contain fructose or glucose, preferably to contain both fructose and glucose. Among other monosaccharides, fructose manifests the effect of inhibiting the hemolytic activity of glycerol when it is added in combination with glycerol to the dialysis solution for peritoneal dialysis. At present, no use is found for fructose in the field of dialysis. In the field of transfusion, fructose has already found utility. It warrants high safety unless the dose thereof is abnormally increased. Generally, the occurrence of fructose in an amount of about 0.5 to 5 mg/dl is recognized in the live blood. Insulin has no part to play in the incorporation of fructose into the cells. In the liver of a test animal as a model of hepatic failure, fructose is utilized more than glucose. In the case of fructose injected into the veins, although about 30% of the amount of fructose injected manifests itself in the form of blood sugar, the added fructose causes no appreciable change in the blood sugar value. Thus, fructose is highly effective in a patient suffering from abnormal metabolism. Glucose is not as effective in inhibiting the hemolytic activity of glycerol as fructose when it is added in combination with glycerol to the dialytic solution for peritoneal dialysis. It, however, has been long used as an osmotic pressure regulating agent in the dialytic soluiton for peritoneal dialysis. We have found in a study that when glucose is contained in the dialytic solution for peritoneal dialysis at least in the concentration in which glucose is normally present in the living body (about 100 mg/dl), the glucose brings about a highly advantageous effect in the preservation of vital balance.

The dialytic solution for peritoneal dialysis may be in a varying percentage composition because the mobility varies from one patient to another, because the ability of treatment varies among the substances to be added, and further because most patients in need of peritoneal dialysis involve a qualitative or quantitative abnormality in lipid metabolism. The glycerol and the monosaccharide as osmotic pressure regulating agents are added in such amounts that the osmotic pressure of the produced dialytic solution for peritoneal dialysis will reach a prescribed level within the range of 280 to 700 mOsm/lit. Generally, the amount of glycerol is in the range of 0.5 to 40 g/lit., preferably 1.0 to 21 g/lit., and that of saccharide in the range of 0.005 to 78 g/lit., preferably 0.01 to 40 g/lit. More desirably, the monosaccharide is contained in an amount of not less than 1 w/v % based on the amount of glycerol. If the amount of the monosaccharide cannot be expected to manifest an effect of preventing the hemolytic activity. If the monosaccharide is added in an extremely large amount as an osmotic pressure regulating agent, there ensues the undesirable possibility that the patient will be forced to take in an excessive energy source. When a plurality of monosaccharides are added, it is desirable that the amount of glycerol will be in the range of 0.5 to 40 g/lit., preferably 1.0 to 21 g/lit., the amount of each of the monosaccharides in the range of 0.005 to 78 g/lit., preferably 0.01 to 40 g/lit., and the total amount of the monosaccharides in the range of 0.005 to 78 g/lit., preferably 0.01 to 40 g/lit. When a plurality of monosaccharides are added as described above, it is permissible that the content of each of the monosaccharides will be decreased so as to lessen the burden imposed on the patient. Particularly the dialytic solution of this invention for peritoneal dialysis can be expected to bring about the best effect when it contains glycerol in an amount 0.5 to 40 g/lit., preferably 1.0 to 21 g/lit., glucose in an amount of 0.005 to 78 g/lit., preferably 0.01 to 40 g/lit., and fructose in an amount of 0.005 to 78 g/lit., preferably 0.01 to 40 g/lit.

In the composition of the dialytic solution of this invention for peritoneal dialysis, various electrolytes are in concentrations conforming to the well-known requirements so as to avoid impairing the ion balance adequate for the living body. For example, the dialytic solution contains 130 to 140 mEq. of $Na^+$ ion, 100 to 140 mEq. of $Cl^-$ ion, 0 to 8 mEq. of $Ca^{2+}$ ion, and 0 to 4 mEq. of $Mg^{2+}$ ion per liter. It further contains, when necessary, 30 to 50 meq. of at least one bicarbonate precursor ion selected from the group consisting of bicarbonate, lactic acid, acetic acid, malic acid, and succinic acid per liter. The bicarbonate precursor ion is added to the dialytic solution of this invention for peritoneal dialysis for the purpose of adjusting the pH of the dialytic solution to a level in the range of about 5.5 to 6.5. If the pH of the dialytic solution of this invention for peritoneal dialysis is not more than 5.5, there ensues the possibility that the dialytic solution introduced into the abdominal cavity will stimulate the living body. If the pH value is close to the vital level (pH 7.4), there is the possibility that the monosaccharides contained as osmotic pressure regulating agents will be seriously decomposed by the intense heat used during the sterilization in an autoclave. When the pH is in the range of about 5.5 to 6.5, the dialytic solution causes absolutely no stimulation on the living body as when the pH is close to the level of the living body and the absolute amount of decomposition caused on the monosaccharides during the sterilization in an autoclave is too small to pose any serious problem.

The ions contained in the prescribed concentrations in the dialytic solution of this invention for peritoneal dialysis can be easily attained by the addition of such popularly used physiological salts as sodium chloride, calcium chloride, sodium lactate, and sodium acetate, such pharmaceutically accepted salts as potassium chloride and magnesium chloride, and free acids.

The dialytic solution of this invention for peritoneal dialysis, in a typical composition, contains 5.53 g of sodium chloride (NaCl), 0.52 g of calcium chloride ($CaCl_2.2H_2O$), 0.07 g of magnesium chloride ($MgCl_2.6H_2O$), and 4.20 g of sodium lactate (8.40 g of 50% by weight sodium lactate) per liter. The amounts of glycerol, fructose, and glucose which the dialytic solution for peritoneal dialysis is presumably required to contain in acquiring electrolyte concentrations (theoretical values) shown in Table 2, pH of 0.5, and an osmotic pressure (theoretical value) of 510 mOsm/lit. are shown in Table 3. The amounts of glycerol, fructose, and glucose which the dialytic solution for peritoneal dialysis is required to contain in acquiring the same electrolyte concentrations and pH as mentioned above and an osmotic pressure (theoretical value) of 350 mOsm/lit. are shown in Table 4. Tables 3 and 4 indicate the amount of glycerol to be required when fructose and glucose are increased or decreased at a fixed proportion.

TABLE 2

| Electrolyte concentration in dialytic solution for peritoneal dialysis | |
|---|---|
| Electrolyte | Concentration (mEq/lit.) |
| $Na^+$ | 132.1 |
| $Ca^{2+}$ | 7.0 |
| $Mg^{2+}$ | 0.7 |
| $Cl^-$ | 110.0 |

TABLE 2-continued

Electrolyte concentration in dialytic solution for peritoneal dialysis

| Electrolyte | Concentration (mEq/lit.) |
|---|---|
| $CH_3CH(OH)COO^-$ | 38.0 |

TABLE 3

Amount of glycerol (g/lit.) required for dialytic solution for peritoneal dialysis having osmotic pressure of 510 mOsm/lit.

| Glucose (g/lit.) | 1.0 | 5.0 | 10.0 | 20.0 | 30.0 | 40.0 |
|---|---|---|---|---|---|---|
| Fluctose (g/lit.) | | | | | | |
| 0 | 20.56 | 18.51 | 15.96 | 10.85 | 5.73 | 0.62 |
| 0.01 | 20.55 | 18.51 | 15.95 | 10.84 | 5.73 | 0.62 |
| 1.0 | 20.05 | 18.00 | 15.45 | 10.33 | 5.22 | 0.11 |
| 10.0 | 15.45 | 13.40 | 10.85 | 5.73 | 0.62 | — |
| 20.0 | 10.33 | 8.92 | 5.73 | 0.62 | — | — |
| 30.0 | 5.22 | 3.18 | 0.62 | — | — | — |
| 40.0 | 0.11 | — | — | — | — | — |

TABLE 4

Amount of glycerol (g/lit.) required for dialysis solution for peritoneal dialysis having osmotic pressure of 350 mOsm/lit.

| Glucose (g/lit.) | 1.0 | 3.0 | 6.0 | 9.0 | 12.0 |
|---|---|---|---|---|---|
| Fluctose (g/lit.) | | | | | |
| 0 | 5.84 | 4.81 | 3.28 | 1.75 | 0.21 |
| 0.01 | 5.83 | 4.81 | 3.28 | 1.74 | 0.21 |
| 0.1 | 5.79 | 4.76 | 3.23 | 1.70 | 0.16 |
| 1.0 | 5.33 | 4.30 | 2.77 | 1.24 | — |
| 2.5 | 4.56 | 3.54 | 2.00 | 0.47 | — |
| 5.0 | 3.28 | 3.26 | 0.73 | — | — |
| 10.0 | 0.725 | — | — | — | — |

Now, the present invention will be described more specifically below with reference to working examples.

EXAMPLES 1-2 AND CONTROLS 1-2 (HEMOLYTIC TEST)

Dialytic solutions, A (Example 1) and B (Example 2), for peritoneal dialysis having compositions shown in Table 5 were prepared. Separately, a physiological saline water, a glucose CAPD solution "CAPD-400" (product of Terumo Kabushiki Kaisha) (Control 1), and a glycerol CAPD solution (Control 2), having compositions shown in Table 1 were prepared. In an environment of 23±1° C. of temperature, 60±10% of humidity, and 12 hours of illumination time, 130 male rats of Wistar species 6 weeks of age (purchased from Shizuoka Laboratory Animal Center) were kept under preliminary breeding for one week. Water and feed were left to be taken freely by the animals. After the preliminary breeding, the rats were divided into 13 lots (each of 10 rats). To the individual rats of each lot, the aforementioned test solutions were intra-abdominally given in a fixed dose of 40 ml/kg with a syringe using a 25 G needle. The rats were anesthesized 60 minutes after the use of the test solutions. Blood was extracted from their abdominal aortas and were centrifuged to obtain serums. The serums were tested for free hemoglobin concentration in accordance with the Nishikaze method (Akira Nishikaze: "New Method for Determination of Blood Oxidized Hemoglobin," March of Medicine, 56, 644, 1966), with necessary modifications. The results of the test are shown in Table 6, as sorted by the presence or absence of residual error in the amounts of serumal free hemoglobin found by comparison between the lot of rats given the physiological saline water and the various lots of rats given the test solutions.

TABLE 5

| Composition | Physiological saline water | Dialytic solution A (Example 1) | | | | Dialytic solution B (Example 2) | | | | | | Glucose CAPD solution (Control 1) | Glycerol CAPD solution (Control 2) |
|---|---|---|---|---|---|---|---|---|---|---|---|---|---|
| | | A1 | A2 | A3 | A4 | B1 | B2 | B3 | B4 | B5 | B6 | | |
| Glycerol (g/lit) | — | 5.8 | 1.0 | 20.6 | 1.0 | 5.8 | 1.0 | 1.0 | 20.5 | 1.0 | 1.0 | — | 20.44 |
| Glucose (g/lit) | — | 1.0 | 10.5 | 1.0 | 39.3 | 1.0 | 10.5 | 1.0 | 1.0 | 39.3 | 1.0 | 40.00 | — |
| Fluctose (g/lit) | — | — | — | — | — | 0.058 | 0.01 | 9.51 | 0.21 | 0.01 | 38.3 | — | — |
| $Na^+$ ion (mEq/lit) | 154 | 135 | 135 | 135 | 135 | 135 | 135 | 135 | 135 | 135 | 135 | 135 | 135 |
| $Cl^-$ ion (mEq/lit) | 154 | 105.5 | 105.5 | 105.5 | 105.5 | 105.5 | 105.5 | 105.5 | 105.5 | 105.5 | 105.5 | 105.5 | 105.5 |
| $Ca^{2+}$ ion (mEq/lit) | — | 4.0 | 4.0 | 4.0 | 4.0 | 4.0 | 4.0 | 4.0 | 4.0 | 4.0 | 4.0 | 4.0 | 4.0 |
| $Mg^{2+}$ ion (mEq/lit) | — | 1.5 | 1.5 | 1.5 | 1.5 | 1.5 | 1.5 | 1.5 | 1.5 | 1.5 | 1.5 | 1.5 | 1.5 |
| Lactate ion (mEq/lit) | — | 35 | 35 | 35 | 35 | 35 | 35 | 35 | 35 | 35 | 35 | 35 | 35 |
| pH | 4.5-7.0 | about 5.5 | about 5.5 | about 5.5 | about 5.5 | about 5.5 | about 5.5 | about 5.5 | about 5.5 | about 5.5 | about 5.5 | about 5.5 | about 5.5 |
| Osmotic pressure (mOsm/lit) | 308 | 350 | 350 | 510 | 510 | 350 | 350 | 350 | 510 | 510 | 510 | about 500 | about 500 |

TABLE 6

| Lot | | Number of animals | Seramal free hemoglobin, Mean + S.E. (mg/dl) |
|---|---|---|---|
| Physiological saline water | | 10 | 8.090 ± 0.348 |
| Dialytic solution | A1 | 10 | 8.290 ± 0.310 |
| " | A2 | 10 | 8.320 ± 0.295 |
| " | A3 | 10 | 8.770 ± 0.345 |
| " | A4 | 10 | 8.540 ± 0.369 |
| " | B1 | 10 | 8.480 ± 0.354 |
| " | B2 | 10 | 8.240 ± 0.346 |
| " | B3 | 10 | 8.180 ± 0.354 |
| " | B4 | 10 | 8.590 ± 0.338 |
| " | B5 | 10 | 8.120 ± 0.346 |
| " | B6 | 10 | 8.100 ± 0.356 |
| Glucose CAPD solution | | 10 | 8.350 ± 0.358 |
| Glycerol CAPD solution | | 10 | 10.250** ± 0.344 |

**: Significantly large amount of serumal free hemoglobin as compared with the lot given the physiological saline water ($P < 0.01$).

EXAMPLE 3

Dialytic solutions for peritoneal dialysis containing 17.89 g of glycerol and 5.00 g of glucose per lit. and having varying pH values (between 5.0 and 8.0, as graduated by intervals of 0.5) were prepared. These dialytic solutions were sterilized in an autoclave at a temperature of 121° C. and pressure of 1 kg/cm² for 40 minutes. After the sterilization, they were tested for glucose concentration and pH, with the results compared with those obtained before the sterilization. The results are shown in Table 7 and FIG. 1.

CONTROL 3

Dialytic solutions (osmotic pressure 510 mOsm/lit.) containing 40.00 g of glucose per lit. and having varying pH values similar to Example 3 were prepared. They were sterilized in an autoclave similarly to Example 3 and tested for glucose concentration and pH before and after the sterilization. The results are shown in Table 7 and FIG. 1.

TABLE 7

Effect of sterilization in autoclave upon dialytic solution

| | pH before sterilization | | | | | | |
|---|---|---|---|---|---|---|---|
| | 5.0 | 5.5 | 6.0 | 6.5 | 7.0 | 7.5 | 8.0 |
| Change in amount of glucose (mg/dl)*1 | | | | | | | |
| Example 3 | 12 | 28 | 44 | 64 | 117 | 161 | 203 |
| Control 3 | 34 | 157 | 258 | 352 | 315 | 640 | 774 |
| Change in pH*2 | | | | | | | |
| Example 3 | 0.05 | 0.05 | 0.20 | 0.45 | 0.80 | 1.00 | 1.40 |
| Control 3 | 0.05 | 0.25 | 0.65 | 1.15 | 1.60 | 2.05 | 2.50 |

*1: (Change in amount of glucose) = (Glucose concentration before sterilization) − (Glucose concentration after sterilization)
*2: (Change in pH) = [−(pH before sterilization) − (pH after sterilization)]

REFERENTIAL TEST

Effect of pH on test animal

Dialytic solutions (osmotic pressure about 500 mOsm/lit.) containing 4 W/V% of glucose, 135 mEq/lit. of Na⁺ ion, 4 mEq/lit. of Mg²⁺ ion, and 105.5 mEq/lit. of Cl⁻ ion and adjusted to varying pH values (between 3 and 7, as graduated by 10 intervals) with lactic acid or a 10% sodium hydroxide solution were prepared.

To mice (ddY, male, 4 weeks of age), the dialytic solutions mentioned above were intra-abdominally given at a fixed dose of 1 ml/mouse 10 minutes after the use of the dialytic solutions, the mice were placed under observation as to the number of writhings and the symptoms. The results are shown in Table 8.

TABLE 8

Effect of pH on test animal

| Lot | Number of mice | pH of dialytic solution used | Number of writhings, mean (per minute) | Finding by observation |
|---|---|---|---|---|
| A | 2 | 3 | 4.5 | Loss of spontaneous movement observed. Trend to loss of spontaneous movement observed. |
| B | 2 | 4 | 0 | No marked change observed. |
| C | 2 | 5 | 0 | No marked change observed. |
| D | 2 | 6 | 0 | No marked change observed. |
| E | 1 | 7 | 0 | No marked change observed. |

As described above, the dialytic solution of the present invention for peritoneal dialysis is characterized by containing glycerol and a monosaccharide as osmotic pressure regulating agents for the regulation of the osmotic pressure to a level necessary for the removal of water. When it is used for peritoneal dialysis on patients suffering from renal insufficiently or intoxication with a poison, therefore, it avoids absorbing excess monosaccharide unlike the conventional dialytic solution containing glucose alone as an osmotic pressure regulating agent and precludes the problems of increased blood sugar value, corpulence, abnormal metabolism of saccharide and lipid, arteriosclerosis, and complication of diseases ascribable to absorption of excess monosaccharide and, unlike the conventional dialytic solution containing glycerol alone as an osmotic pressure regulating agent, eliminates the possibility of hemolysis by glycerol owing to the presence of the monosaccharide. Since the dialytic solution of this invention for peritoneal dialysis is highly safe on the living body, it can be used advantageously for protracted administration or sustained administration as by CAPD. These desirable effects of the dialytic solution are particularly conspicuous when it contains, as the monosaccharide, a human metabolic monosaccharide, desirably fructose or glucose, and more desirably both fructose and glucose, when the glycerol and the monosaccharide are contained respectively in the range of 0.5 to 40 g/lit. and in the range of 0.005 to 78 g/lit., preferably the glycerol in the range of 1.0 to 21 g/lit., the glucose in the range of 0.01 to 40 g/lit., and the fructose in the range of 0.01 to 40 g/lit., and when the pH of the dialytic solution falls in the range of 5.5 to 6.5.

What is claimed is:

1. A dialytic solution for peritoneal dialysis, said dialytic solution comprising 0.5 to 40 g/liter of glycerol, 0.005 to 78 g/liter of glucose, 0.005 to 78 g/liter of fructose as osmotic pressure regulating agents for regulating the osmotic pressure to a level necessary for the removal of the water.

2. The dialytic solution according to claim 1 further including Na⁺ ion in an amount of 130 to 140 mEq/liter, Cl⁻ ion in an amount of 100 to 140 mEq/liter, Ca²⁺ ion in an amount of 0 to 8 mEq/liter and Mg²⁺ in an amount of 0 to 4 mEq/liter.

3. The dialytic solution according to claim 1 further including at least one bicarbonate precursor ion selected from the group consisting of bicarbonates, lactic acid, acetic acid, malic acid and succinic acid present in an amount of 30 to 50 mEq/liter.

4. The dialytic solution according to claim 1 wherein said osmotic pressure is in the range of 280 to 700 mOsm/liter.

5. The dialytic solution according to claim 1, wherein the pH is in the range of 5.5 to 6.5.

* * * * *